US008679173B2

(12) United States Patent
Dierking et al.

(10) Patent No.: US 8,679,173 B2
(45) Date of Patent: Mar. 25, 2014

(54) HYBRID STENT AND METHOD OF MAKING SUCH A STENT

(75) Inventors: W. Kurt Dierking, Louisville, KY (US); Alan R. Leewood, Lafayette, IN (US); Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 100 days.

(21) Appl. No.: 13/257,073

(22) PCT Filed: Mar. 15, 2010

(86) PCT No.: PCT/US2010/027281
§ 371 (c)(1),
(2), (4) Date: Oct. 4, 2011

(87) PCT Pub. No.: WO2010/107681
PCT Pub. Date: Sep. 23, 2010

(65) Prior Publication Data
US 2012/0029624 A1 Feb. 2, 2012

Related U.S. Application Data

(60) Provisional application No. 61/160,485, filed on Mar. 16, 2009.

(51) Int. Cl.
*A61F 2/82* (2013.01)
(52) U.S. Cl.
USPC .................................. 623/1.32; 623/1.44
(58) Field of Classification Search
USPC ...................... 623/1.32–1.34, 1.44
See application file for complete search history.

(56) References Cited

U.S. PATENT DOCUMENTS

| 5,405,377 A | 4/1995 | Cragg .......................... 623/1 |
| 5,607,442 A | 3/1997 | Fischell et al. ................ 606/191 |
| 5,776,162 A | 7/1998 | Kleshinski .................... 606/198 |
| 6,053,943 A | 4/2000 | Edwin et al. ................. 623/1.25 |
| 6,071,307 A | 6/2000 | Rhee et al. ................... 623/1.13 |
| 6,174,329 B1 | 1/2001 | Callol et al. ................. 623/1.34 |

(Continued)

FOREIGN PATENT DOCUMENTS

WO WO 02/36045 5/2002 ............... A61F 2/06

OTHER PUBLICATIONS

International Search Report dated May 27, 2010, International Application No. PCT/US2010/027281, filed Mar. 15, 2010 (3 pages).

*Primary Examiner* — Thomas J Sweet
*Assistant Examiner* — Rebecca Preston
(74) *Attorney, Agent, or Firm* — Brinks Gilson & Lione

(57) ABSTRACT

A hybrid stent (100) includes at least one resilient ring (105) comprising a superelastic wire (102) formed in a sinusoidal pattern of alternating crests (110) and troughs (115) about a circumference of the ring (105). A plurality of malleable cannula segments (120) overlie the superelastic wire at the crests and troughs. Each of the cannula segments (120) includes a bend (125) and has an inner diameter sized to allow relative motion between the wire (102) and the cannula segment (120). The hybrid stent (100) may also include a plurality of gaps (130), where each gap (130) is defined by a spacing between opposing cannula segments (120). Deformation of the malleable cannula segments (120) dominates a response of the stent to substantially uniform radial forces, and deformation of the resilient ring (105) dominates a response of the stent to radially nonuniform crushing forces.

17 Claims, 9 Drawing Sheets

(56) References Cited

U.S. PATENT DOCUMENTS

| | | | |
|---|---|---|---|
| 6,241,691 B1 | 6/2001 | Ferrera et al. | 600/585 |
| 6,632,223 B1 | 10/2003 | Keane | 606/41 |
| 6,890,350 B1 | 5/2005 | Walak | 623/1.15 |
| 6,974,472 B2 | 12/2005 | Hong et al. | 623/1.15 |
| 2006/0259137 A1 | 11/2006 | Artof et al. | 623/2.18 |
| 2008/0046071 A1* | 2/2008 | Pavcnik | 623/1.24 |
| 2008/0319528 A1* | 12/2008 | Yribarren et al. | 623/1.15 |
| 2009/0138068 A1* | 5/2009 | West et al. | 623/1.13 |
| 2010/0211163 A1* | 8/2010 | Gershlick | 623/1.18 |

\* cited by examiner

HYBRID STENT AND METHOD OF MAKING SUCH A STENT

RELATED APPLICATIONS

The present patent document is the national stage of International Application No. PCT/US2010/027281, which was filed on Mar. 15, 2010, and which claims the benefit of the filing date under 35 U.S.C. 119(e) of U.S. Provisional Patent Application Serial No. 61/160,485, which was filed on Mar. 16, 2009, both of which are hereby incorporated by reference in their entirety.

FIELD OF THE INVENTION

The present disclosure is related generally to implantable medical devices and more particularly balloon-expandable stents.

BACKGROUND ART

Stents are generally designed as tubular support structures that can be used in a variety of medical procedures to treat blockages, occlusions, narrowing ailments and other problems that restrict flow through body vessels. An expandable stent is radially compressed to a low-profile configuration for passage through a body vessel, and then, once in position at a treatment site, the stent may be radially expanded to a larger-diameter deployment configuration to contact and support the inner wall of the vessel. Such stents are generally classified as either balloon-expandable or self-expanding. Balloon-expandable stents expand in response to the inflation of a balloon, while self-expanding stents expand spontaneously when released from a delivery device.

Balloon-expandable stents may provide the benefits of high radial stiffness and strength, minimal recoil, and controlled behavior during expansion. Self-expanding stents may offer the advantages of low-profile delivery and elastic deployment. A self-expanding stent may be crimped by as much as a 3:1 ratio from an expanded to a low-profile configuration (e.g., from 10 mm to 7 Fr) and then substantially fully recover the expanded configuration when deployed. Many self-expanding stents are made of superelastic nickel-titanium alloys that can recover strains as high as 8-10%.

The inventors believe a stent that has the attributes of both balloon-expandable and self-expanding stents would be advantageous.

SUMMARY OF THE INVENTION

The present invention seeks to provide an improved implantable medical device and an improved stent structure for an implantable medical device.

According to an aspect of the present invention, there is provided a hybrid stent as specified in claim 1.

According to another aspect of the present invention, there is provided an implantable medical device including a hybrid stent as taught herein.

According to another aspect of the present invention, there is provided a method of making a hybrid stent as specified in claim 19.

A hybrid stent that exploits both plastic and superelastic modes of deformation for deployment and use in a body vessel is described herein. The hybrid stent is plastically deformed for crimping and balloon expansion but exhibits superelastic recovery in response to crushing forces experienced in vivo. The inventors believe the hybrid stent is well-suited to applications in the superficial femoral artery (SFA), the carotid artery, and any other vessels that may be deformed or collapsed by external forces or by internal bodily functions or movement.

The preferred embodiment of hybrid stent includes at least one resilient ring comprising a superelastic wire formed in a sinusoidal pattern of alternating crests and troughs about a circumference of the ring. A plurality of malleable cannula segments overlie the superelastic wire at the crests and troughs. Each of the cannula segments includes a bend and has an inner diameter sized to allow relative motion between at least a portion of the wire and the cannula segment. Deformation of the malleable cannula segments dominates a response of the stent to substantially uniform radial forces, and deformation of the superelastic wire dominates a response of the stent to radially nonuniform crushing forces.

A preferred method of making a hybrid stent includes cutting a malleable continuous cannula into a plurality of cannula segments and deforming each of the cannula segments to include a bend of a desired radius. A superelastic wire is threaded through each of the cannula segments. The superelastic wire is curved so as to bring ends of the superelastic wire into contact, and the ends of the superelastic wire are bonded together to form the hybrid stent. Each of the cannula segments has an inner diameter sized to allow relative motion between the wire and the cannula segment.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
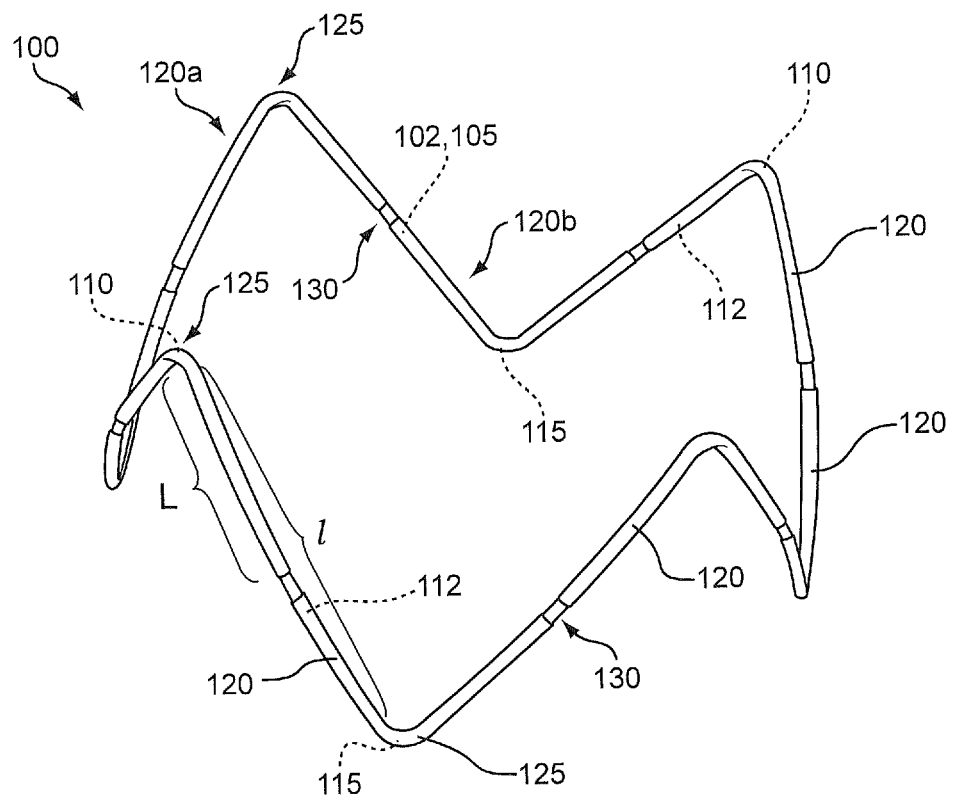
FIG. 1 shows a first embodiment of a hybrid stent including a resilient ring and overlying cannula segments.
Figure 2:
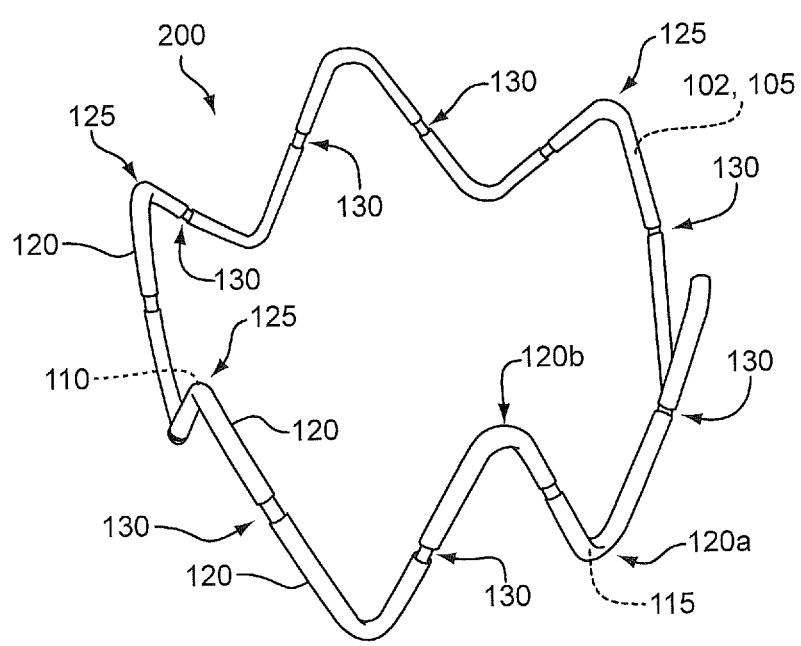
FIG. 2 shows a second embodiment of a hybrid stent including a resilient ring and overlying cannula segments.

FIGS. 1 and 2 are representations of exemplary hybrid stents 100, 200 in a radially expanded configuration. The exemplary stents 100, 200 include a resilient ring 105 comprising a superelastic wire 102 formed in a sinusoidal pattern having alternating crests 110 and troughs 115 about a circumference of the ring 105. Portions of the superelastic wire 102 that extend between the crests 110 and troughs 115 may be referred to as struts 112 of the hybrid stent 100, 200. The hybrid stent 100 of FIG. 1 includes four crests 110 and four troughs 115, while the hybrid stent 200 of FIG. 2 includes six crests 110 and six troughs 115.

The hybrid stents 100, 200 also include discrete, malleable cannula segments 120 overlying the superelastic wire 102 at the crests 110 and troughs 115. Each of the cannula segments 120 includes a bend 125 to accommodate the curvature of the crests 110 and troughs 115 and has an inner diameter sized to allow for relative motion between the wire 102 and the segment 120. The stents 100, 200 also include a plurality of gaps 130 between opposing cannula segments 120 that expose the underlying superelastic wire 102. Each gap 130 is defined by a spacing between adjacent and oppositely disposed cannula segments 120 (e.g., between opposing cannula segments 120a and 120b).

Plastic deformation of the malleable cannula segments 120 dominates the response of the stent 100, 200 to radial forces, particularly the substantially uniform radial forces applied during crimping and deployment, whereas the elasticity of the resilient ring 105 dominates the response of the stent 100, 200 to crushing forces, as will be discussed in greater detail below.

The resilient ring 105 may be formed from a superelastic wire 102 having ends joined together to define the circumference of the ring 105. Preferably, the superelastic wire 102 is a round wire. Alternatively, the resilient ring may be formed from a seamless superelastic wire, such as a flat wire cut from a thin-walled tube.

The superelastic wire 102 is preferably fabricated from a biocompatible shape memory alloy that can "remember" and elastically recover a previous shape when an applied stress is removed. The shape memory alloy may be a nickel-titanium alloy (e.g., Nitinol) where the source of the shape recovery is a phase transformation between a lower temperature phase (martensite) and a higher temperature phase (austenite). The elastic spring back of superelastic nickel-titanium alloys is powered by a reverse phase transformation from martensite to austenite, during which strains of up to about 8-10% may be recovered. Slightly nickel-rich Nitinol alloys including, for example, about 51 at. % Ni and about 49 at. % Ti are known to be useful for stents and other medical devices which behave superelastically at body temperature. More generally, nickel-titanium alloys including 50.6-50.8 at. % Ni and 49.2-49.4 at. % Ti are known to be medical grade Nitinol alloys and may be suitable for the superelastic wire. The nickel-titanium alloy may also include one or more additional alloying elements.

It is to be appreciated that Nitinol is a preferred material for the shape memory part of the stent and that other materials could also be used, such as other shape memory alloys and metals, as well as shape memory polymers and other materials.

The malleable cannula segments 120 overlying the superelastic wire 102 are preferably formed of a strong but ductile metal or alloy, such as stainless steel. Generally speaking, the metal or alloy of the malleable cannula segments 120 includes one or more transition metal elements, such as, for example, Fe, Co, Cr, Mo, Ti, Au, Pt, Pd, or others.

The inventors have employed finite element analysis (FEA) using Abaqus/Standard 6.8-1 software to model the behavior of an exemplary hybrid stent including a superelastic ring and overlying malleable cannula segments under radially uniform and nonuniform loads (e.g., crimping versus crushing forces). From the FEA simulations, it is possible to determine the level of plastic strain and/or stress in the cannula segments and the superelastic ring during deformation of the hybrid stent. Stress or strain contours reveal local regions that undergo the most significant deformation.

Figure 3:
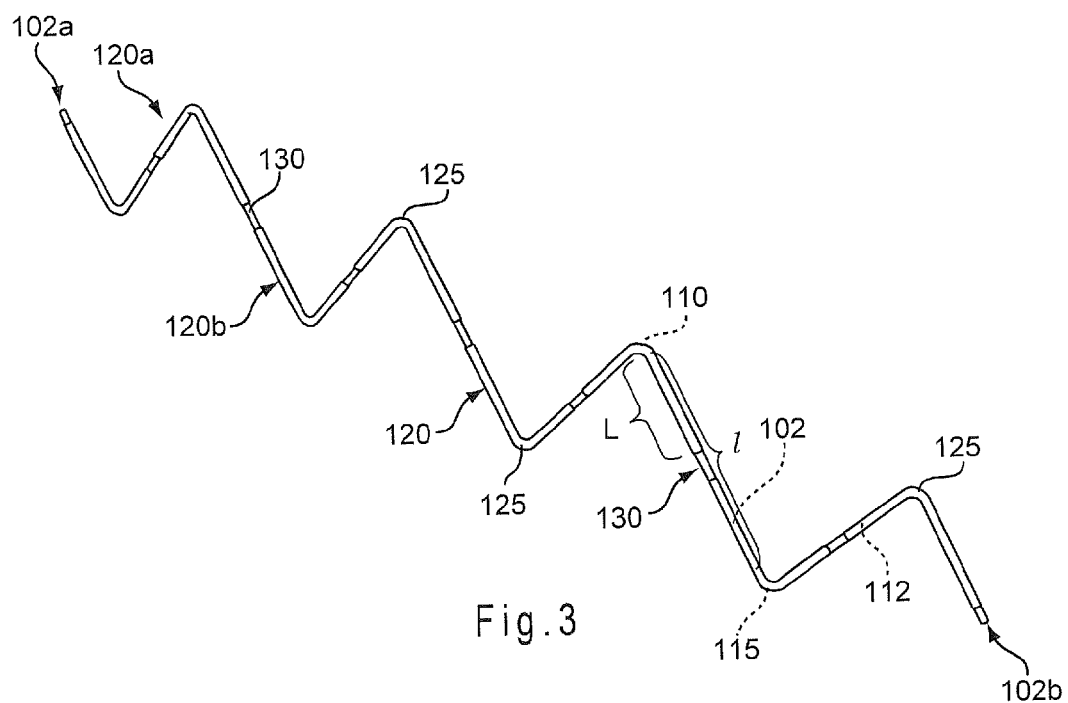
FIG. 3 shows a superelastic wire with overlying cannula segments prior to forming the hybrid stent.

Referring to FIG. 3, the exemplary hybrid stent 100 of FIG. 1 was simulated from a superelastic wire 102 with four crests 110 and four troughs 115 along the length thereof. Ends 102a, 102b of the wire 102 were joined to form the resilient ring 105 and define a circumference of the hybrid stent 100, as shown in FIG. 1. Each of the struts 112 extending between the crests 110 and troughs 115 had a length l of 9.5 mm, and the simulated wire 102 had a thickness (diameter) of 0.25 mm. The overlying cannula segments 120 were sized to define gaps 130 of about 0.55 mm between opposing cannula segments 120 and to provide a clearance of about 0.025 mm between the inner diameter of each cannula segment 120 and the outer diameter of the wire 102. It was assumed that the superelastic wire 102 was made of a Nitinol alloy, and a material model for Nitinol which is widely accepted in the medical device community was used in the FEA simulations. The malleable cannula segments 120 were assumed to be made of a stainless steel alloy, and an accepted elasto-plastic material model for stainless steel was employed in the FEA simulations.

Figure 4:
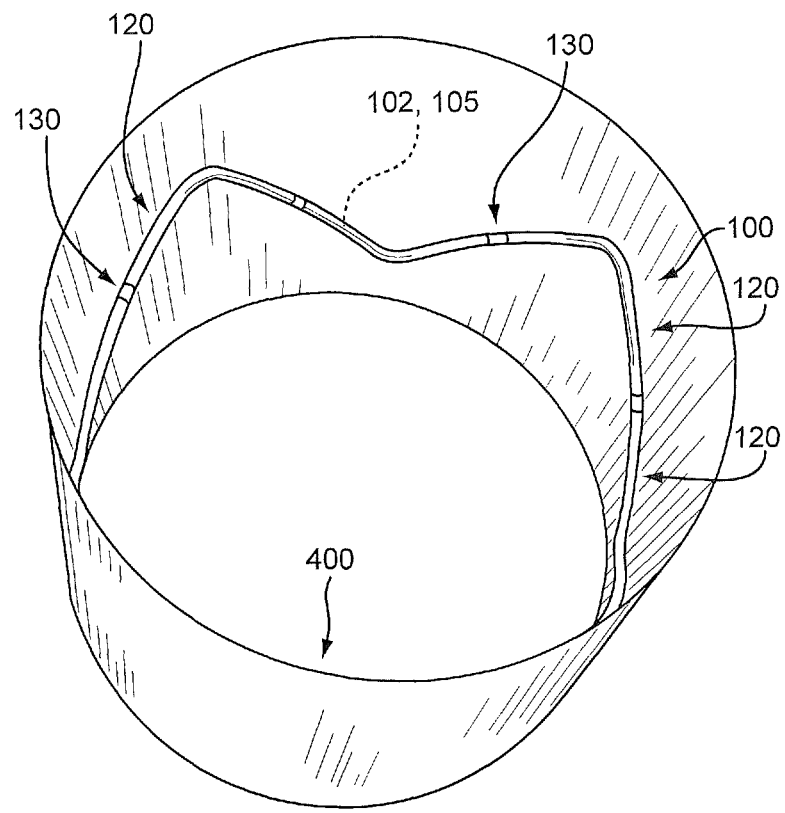
FIG. 4 shows the hybrid stent of FIG. 1 in a crimping apparatus prior to crimping to a reduced diameter configuration.
Figure 5:
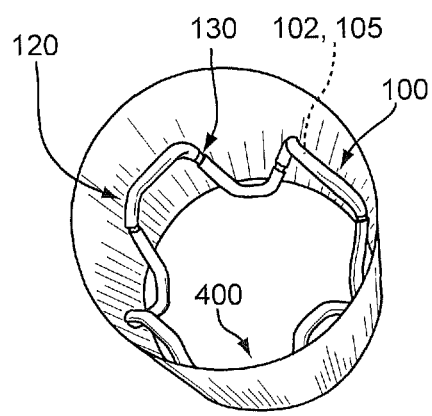
FIG. 5 shows the hybrid stent of FIG. 1 in a crimping apparatus after crimping to a reduced diameter configuration.

FIGS. 4 and 5 show the simulated hybrid stent 100 prior to and after crimping to a reduced-diameter or low-profile configuration for insertion into a body vessel. First, the hybrid stent 100 was placed in a crimping tool 400, as shown in FIG. 4, and then uniform radial forces were applied to compress the hybrid stent 100 to the reduced-diameter configuration, as shown in FIG. 5. The wire-cannula segment interaction was modeled as a sliding (low friction) interface in the FEA simulations.

The compression is achieved primarily by bending at the apices of hybrid stent, where the malleable cannula segments overlie the smaller-diameter superelastic wire. The elastic energy present in the resilient ring is insufficient to counter the plastic energy of the deformed cannula segments; thus, the stent is able to retain the crimped configuration even after removal from the crimping tool.

Figure 6:
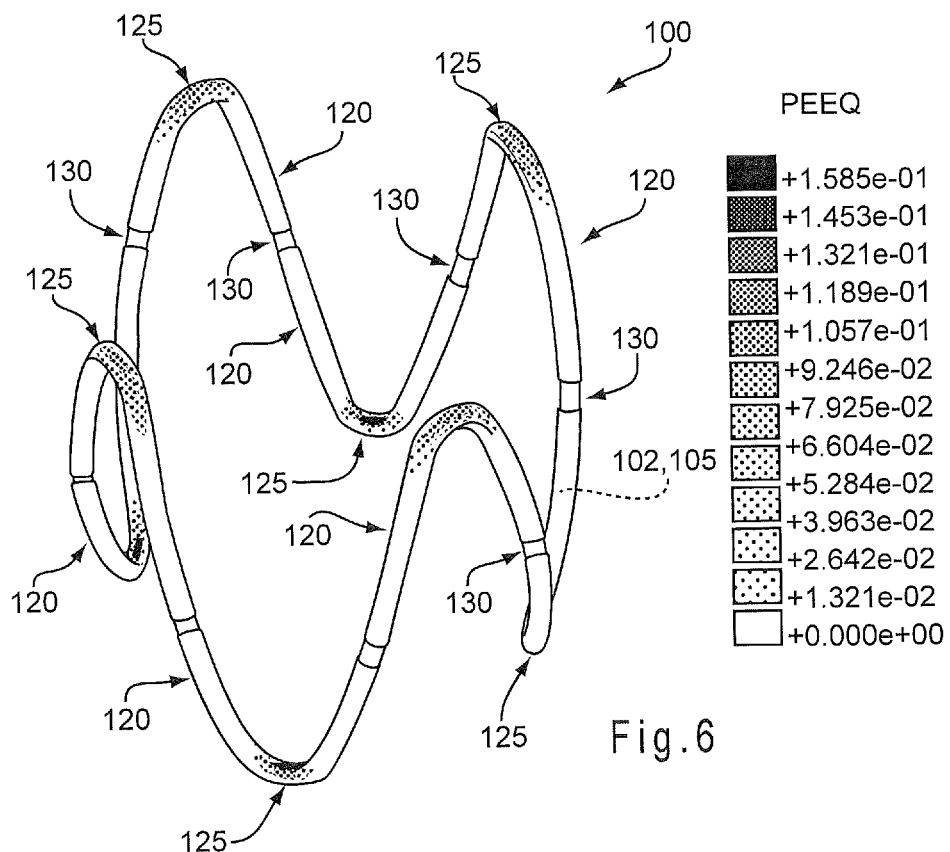
FIG. 6 is a contour plot generated from finite element analysis (FEA) of the hybrid stent of FIG. 5 that shows plastic strain in bends of the cannula segments.
Figure 7:
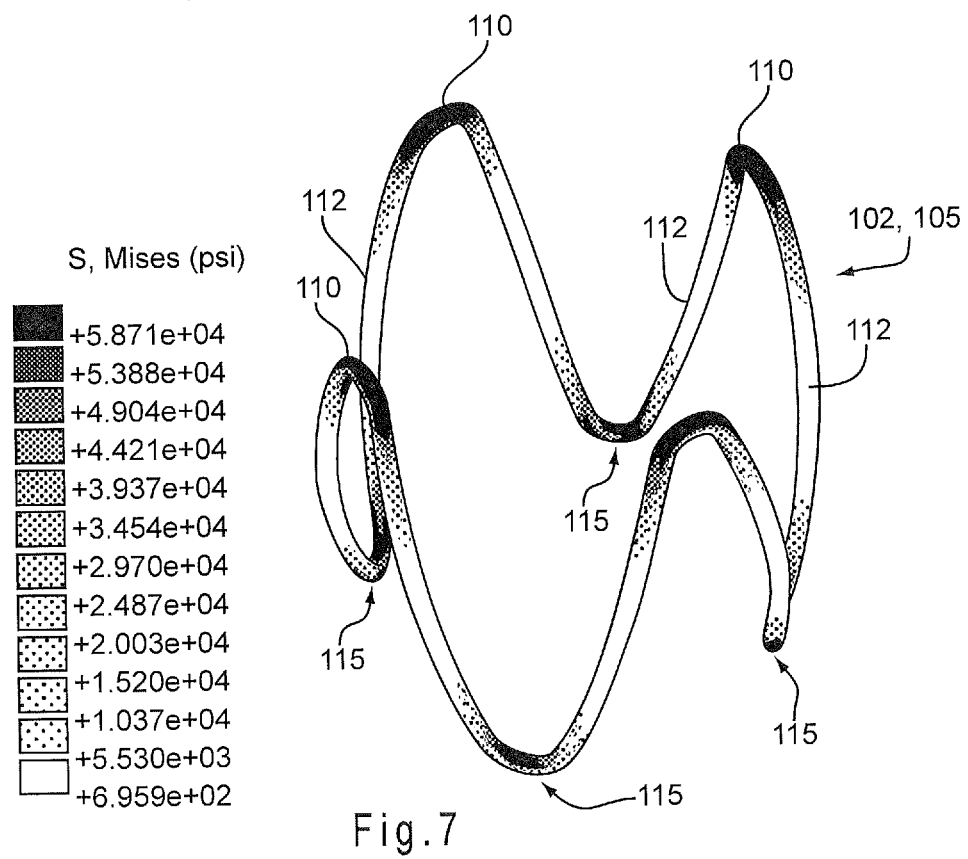
FIG. 7 is a contour plot generated from FEA of the hybrid stent of FIG. 5 that shows the Mises stress in crests and troughs of the superelastic wire.

FIG. 6 is a contour plot generated from the FEA simulations that shows equivalent plastic strain (PEEQ) in the bends or apices 125 of the crimped cannula segments 120. This plastic or permanent deformation is believed to be responsible for locking the hybrid stent 100 in the crimped configuration, despite the elasticity of the underlying superelastic wire 102. FIG. 7 is a contour plot showing the Mises stress (in psi) in the nickel-titanium alloy wire 102 of the resilient ring 105. These stresses are not sufficient to cause the stent 100 to recoil back to its original state. Another factor contributing to the behavior is that Nitinol has about ⅓ the stiffness (Young's modulus) of stainless steel.

Once in the low-profile configuration, the hybrid stent may be transported via an intraluminal delivery system to a treatment site within a body vessel. At the treatment site, the hybrid stent may be radially expanded by a balloon to a deployed configuration.

Figure 8:
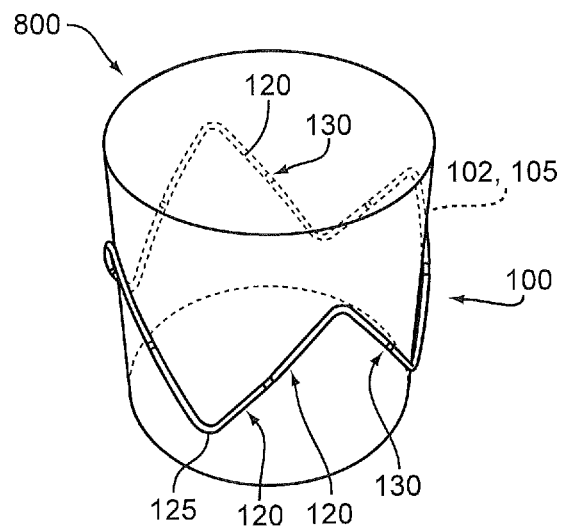
FIG. 8 shows the hybrid stent of FIG. 1 prior to uniform radial expansion.
Figure 9:
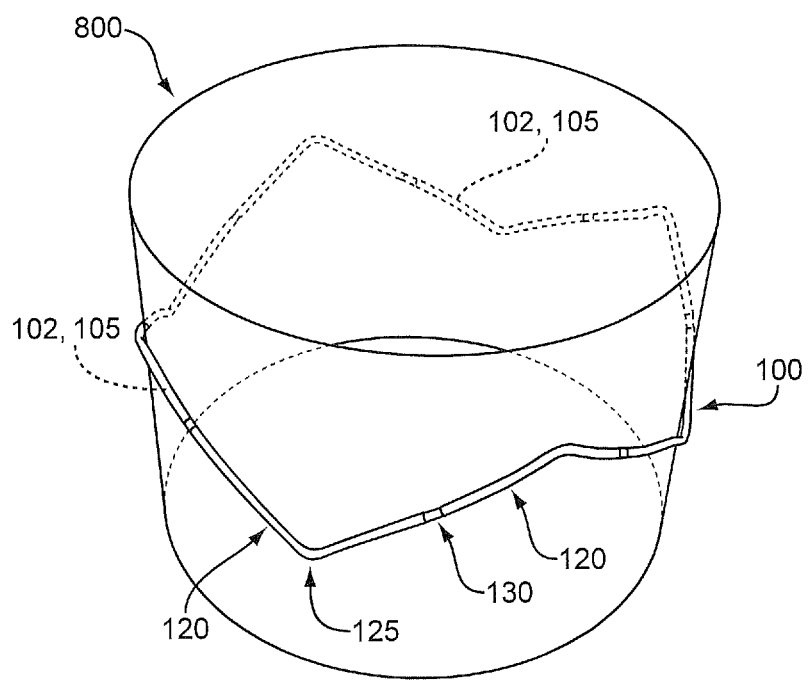
FIG. 9 shows the hybrid stent of FIG. 1 after uniform radial expansion.

FIGS. 8 and 9 are FEA simulations of an exemplary balloon expansion of the hybrid stent 100. The hybrid stent 100 is uniformly expanded from an uncrimped nominal radius of eight units to an expanded radius of twelve units by a means (e.g., a balloon) 800 of supplying a uniform outward radial force. The simulated balloon expansion deforms the hybrid stent 100 in much the same manner as does crimping.

The FEA simulations indicate little change in the hybrid stent at full balloon expansion and after the balloon has been deflated and withdrawn. The expanded configuration is substantially maintained after the expanding force is removed, with the exception of some amount of elastic recoil. For the simulated hybrid stent 100 of FIG. 9, the recoil is about 26%. In practice, the amount of recoil is believed to depend on the material properties of the cannula segments and the resilient ring, as well as on their geometric properties (e.g., diameter, thickness, and/or strut length). Also, the attachment mode of the cannula segments to the superelastic wire (e.g., free sliding versus spot welds) as well as any annealing and forming processes may have an impact.

Figure 10:
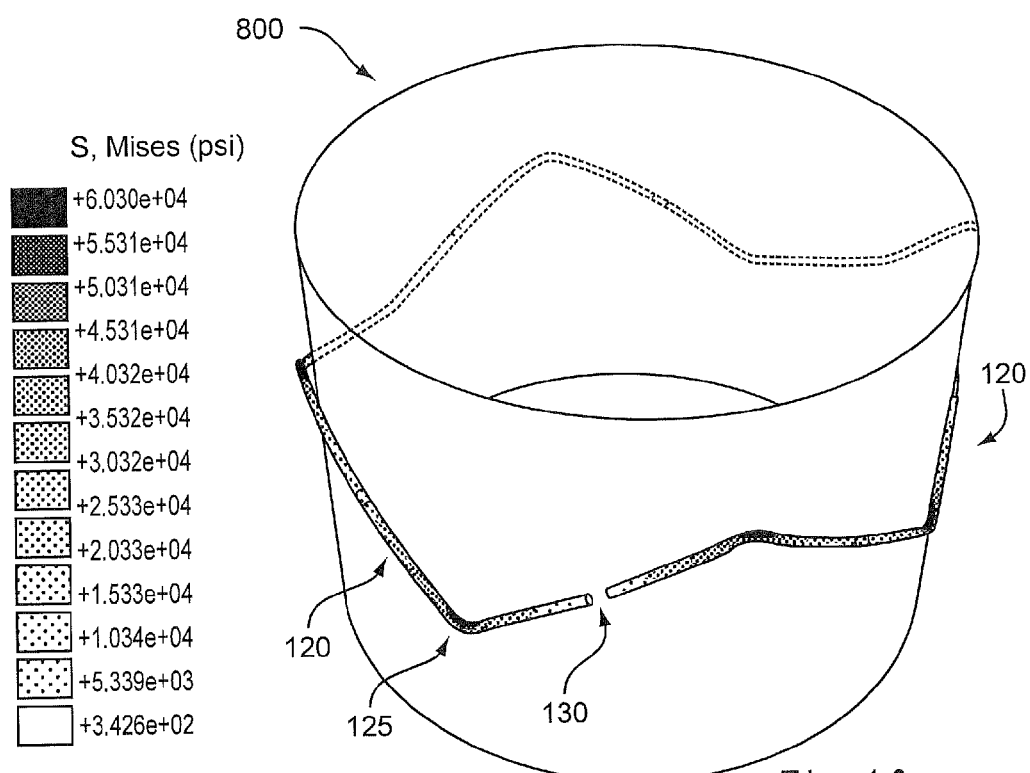
FIG. 10 is a contour plot generated from FEA of the hybrid stent of FIG. 9 that shows plastic strain in the bends of the cannula segments.
Figure 11:
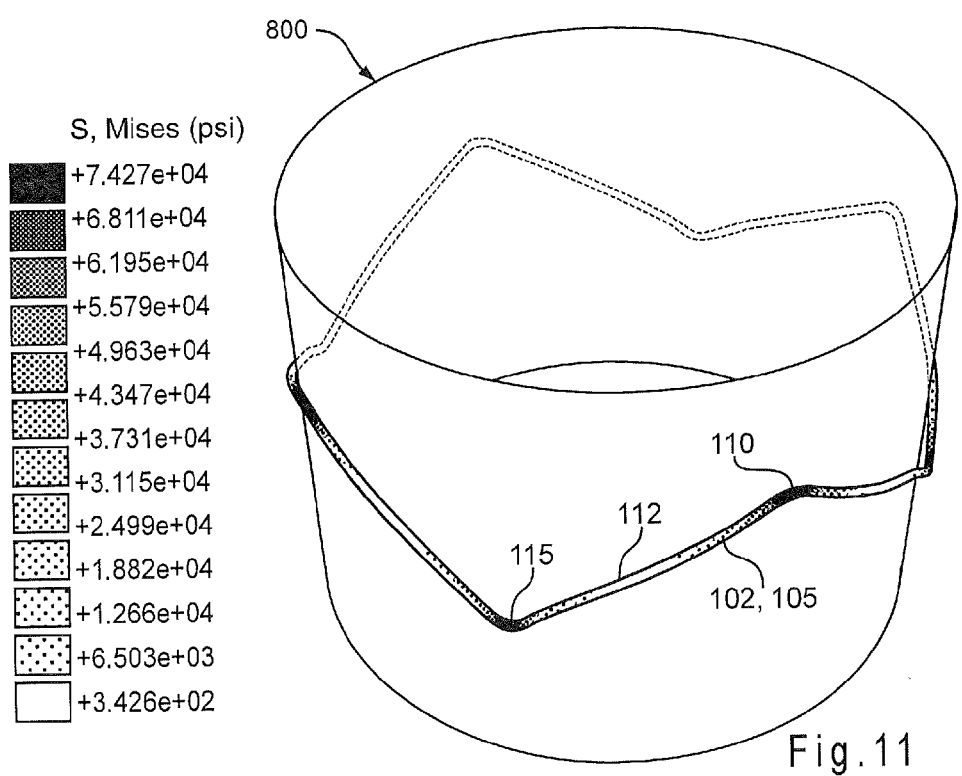
FIG. 11 is a contour plot generated from FEA of the hybrid stent of FIG. 9 that shows the Mises stress in crests and troughs of the superelastic wire.

The contour plot of FIG. 10 reveals that significant plastic deformation occurs in the bends of the malleable cannula segments 120 due to the simulated expansion. The plastic deformation tends to lock the hybrid stent 100 in the expanded configuration (with the exception of the small degree of recoil discussed above). FIG. 11 shows a contour plot of the Mises stress in the superelastic nickel-titanium wire 102 of the resilient ring 105. The stresses in the wire 102 are focused in the bends (crests 110 and troughs 115) as well, but the elastic energy present in the superelastic wire 102 is not sufficient to substantially alter the configuration of the deformed cannula segments 120.

Thus, the hybrid stent 100 is able to maintain the expanded diameter despite the tendency of the resilient ring 105 to elastically recover a previous shape. The inventors believe that any substantially uniform change in the diameter of the hybrid stent 100 is dominated by the plastic deformation of the bends or apices 125 of the malleable cannula segments 120.

In contrast, the elasticity of the resilient ring 105 is exploited when the stent 100 is in use in the body vessel and subjected to crushing forces or other radially nonuniform stresses. In superficial arteries, such as the superficial femoral artery (SFA), for example, the deployed stent 100 may be subjected to crushing loads sufficient to cause conventional balloon-expandable stents to collapse unrecoverably. Thus, in addition to the behavior of the hybrid stent under uniform radial forces during crimping or expansion, the inventors also used FEA to explore the behavior of the hybrid stent under crushing forces, as described below.

Figure 12:
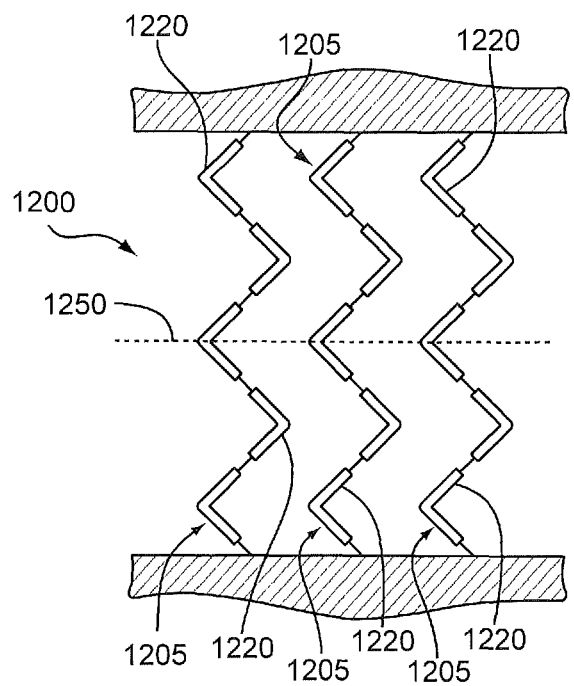
FIGS. 12 and 13 show exemplary stents that include more than one resilient ring comprising a superelastic wire, where each resilient ring includes overlying cannula segments.
Figure 13:
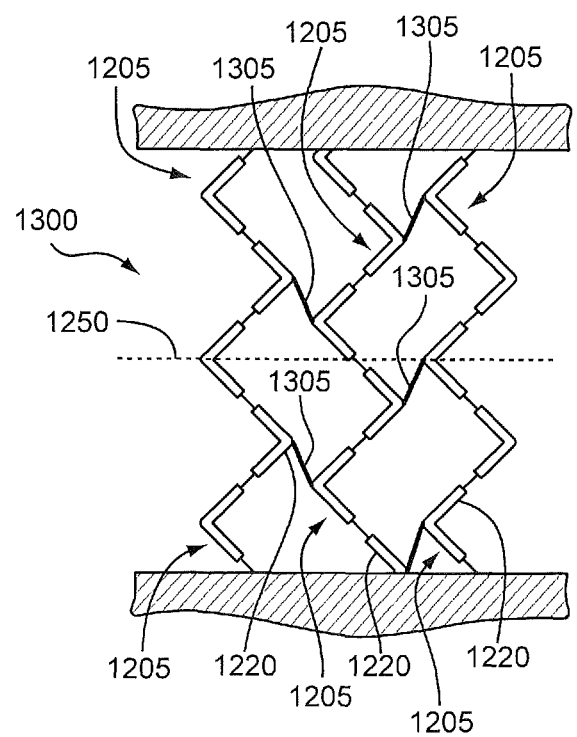

It is important to note that the hybrid stent 100 deployed in the body is not limited to a single ring of superelastic wire. For example, as shown in FIG. 12, the hybrid stent 1200 may include a plurality of the resilient rings 1205 with overlying cannula segments 1220 arranged along a longitudinal axis 1250. Referring to Figure 13, the stent 1300 may also include a number of interconnecting segments 1305 that join longitudinally adjacent rings 1205 (or cannula segments 1220). The interconnecting segments 1305 may be made of a metal or alloy such as stainless steel or Nitinol, according to one embodiment, or the segments 1305 may be made of a biodegradable material.

Figure 14A:
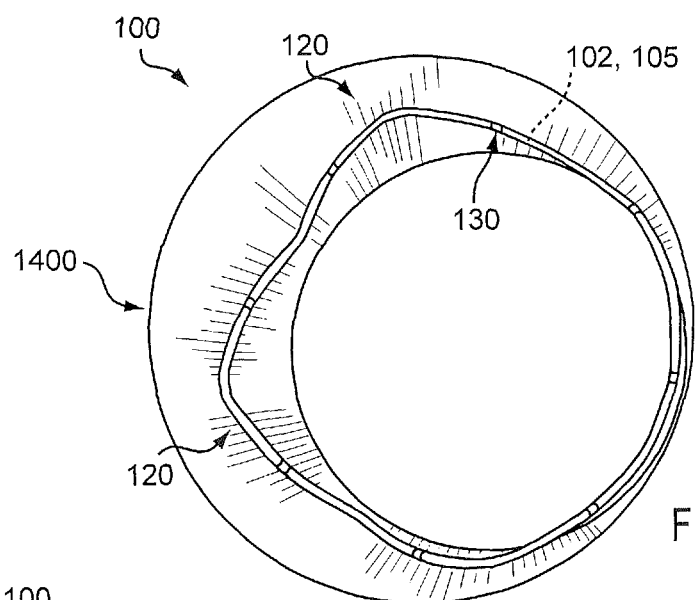
FIGS. 14A-14C show the hybrid stent of FIG. 1 prior to, during, and after exposure to an exemplary crushing load, respectively.

FEA simulations to explore the behavior of the hybrid stent under crushing loads were carried out using the exemplary hybrid stent 100 of FIG. 1. Referring to FIG. 14A, the hybrid stent 100 is placed into an idealized flexible vessel 1400, which is then exposed to a crushing or flattening load (FIG. 14B) intended to simulate the experience of the stent 100 in the SFA or the carotid artery, for example. FIG. 14C shows the hybrid stent 100 after exposure to the load.

Figure 14B:
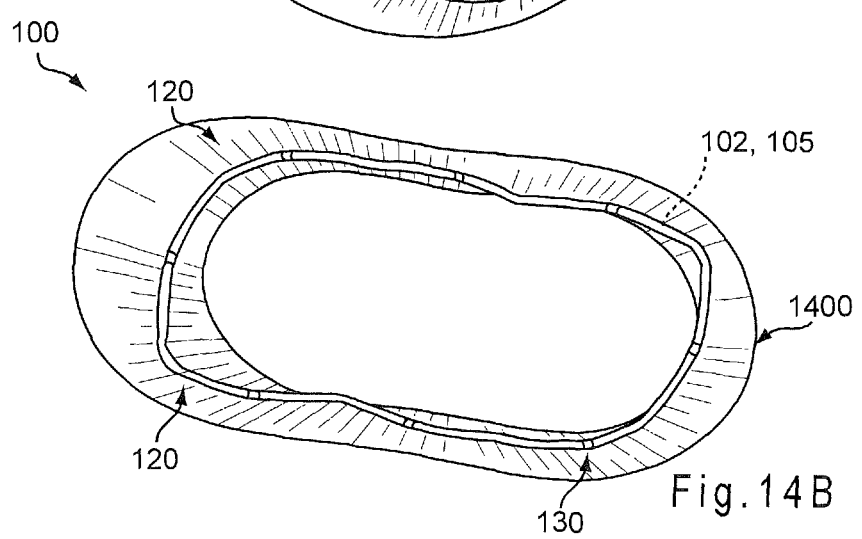
Figure 14C:
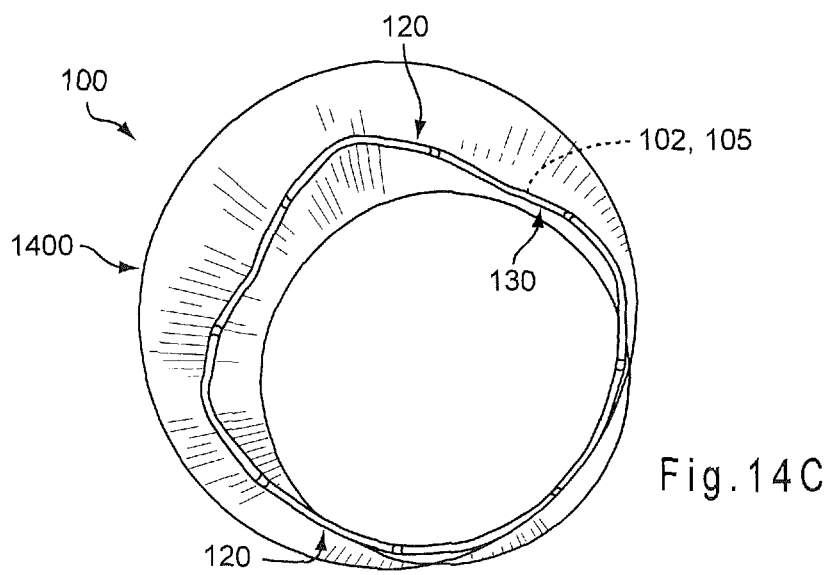

Referring to FIG. 14B, the superelastic wire 102 of the hybrid stent 100 is able to torque or twist between opposing cannula segments 120 in response to the load. The stent 100 thus conforms to the flattened vessel by torsion of the superelastic wire 102 and rotation of at least a portion of the cannula segments about the wire. The gaps 130 between opposing cannula segments 120 and the clearance between the segments 120 and underlying wire 102 facilitate this rotation. Once the load is removed, the flexible vessel 1400 returns to its original cylindrical shape, and the hybrid stent 100 substantially recovers the original undeformed geometry by the elastic spring back capacity of the resilient ring 105, as indicated in FIG. 14C.

Figure 15:
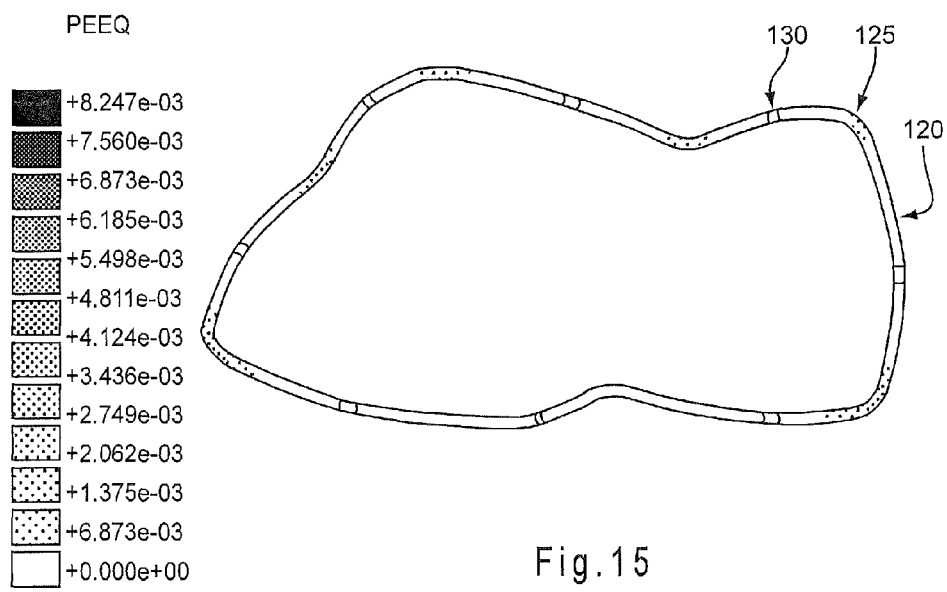
FIG. 15 is a contour plot generated from FEA of the hybrid stent of FIG. 14B that shows plastic strain in the cannula segments.
Figure 16:
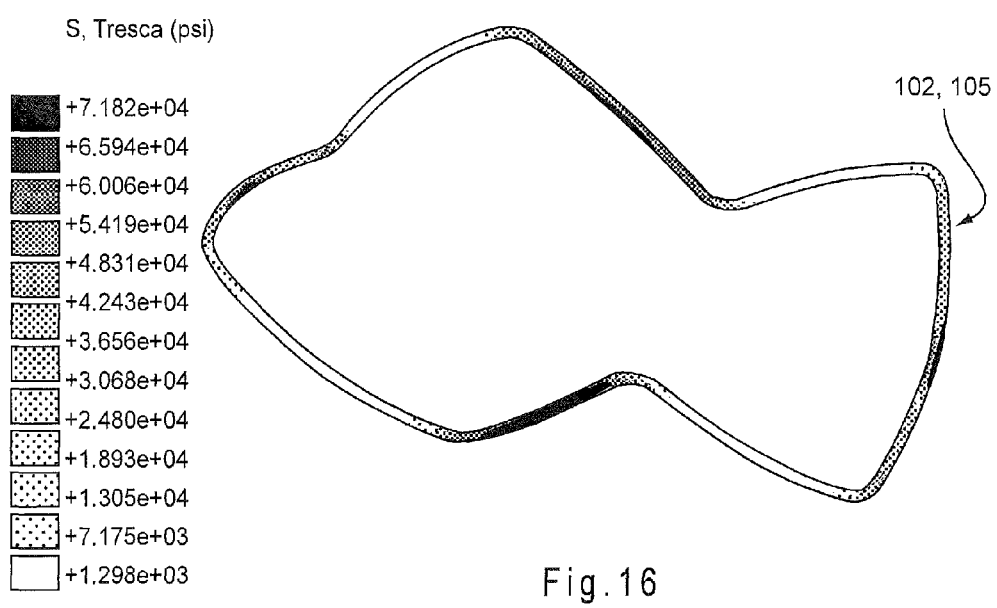
FIG. 16 is a contour plot generated from FEA of the hybrid stent of FIG. 14B that shows shear stress in the superelastic wire.

The contour plots of FIGS. 15 and 16 provide some insight into why the hybrid stent can accommodate such a crushing load and yet completely recoil. FIG. 15 shows equivalent plastic strain (PEEQ) in the cannula segments 120 of the hybrid stent 100 under the flattening load applied in FIG. 14B. There is little or no plastic deformation in the stainless steel cannula segments 120 that is created by the flattening loading modality. Instead, the cannula segments 120 can rotate about the superelastic wire 102 without plastically deforming as the wire 102 twists to accommodate the load. The motion of the cannula segments 120 with respect to the superelastic wire 102 can be attributed to the gaps 130 at the mid-strut regions as well as to the slip-fit between at least portions of the cannula segments 120 and the wire 102. FIG. 16 shows the contour of Tresca (maximum shear) stress in the resilient ring 105, which reveals the torsional shear stresses experienced along mid-strut regions of the nickel-titanium alloy wire 102 (i.e., at the sites of the gaps 130 between the cannula segments 120). When the vessel 1400 returns to its cylindrical shape, the shear stresses in the superelastic wire 102 power the stent 100 back to its original (or near original) annular shape.

The size of the gaps 130 between opposing cannula segments 120 may be minimized so as to maximize the length of the cannula segments 120. Having longer cannula segments 120 may improve the structural stability of the hybrid stent 100 when crimped for delivery or when deployed in the vessel. Accordingly, a minimum gap size may correspond to a spacing between adjacent and oppositely disposed cannula segments 120 that is (merely) sufficient to prevent contact and friction between the opposing segments 120 when the hybrid stent 100 is in use. The gap size may also be substantially larger. For example, each gap 130 may extend over as much as about ⅓ of the length of a strut 112 (the portion of the superelastic wire 102 between an opposing crest and trough). More specifically, the gaps 130 may range in size from about 1% to about 25% of the length of the struts 112. The gaps 130 may be uniform in size across the entire stent 100, or the gaps 130 may vary in size. For example, gaps of a first size A may alternate with gaps of a second size B about the circumference of the hybrid stent. It is also contemplated that the hybrid stent may not include gaps. For example, the cannula segments may have a length such that opposing segments overlap. In this embodiment, the motion of the cannula segments with respect to the superelastic wire as the stent deforms may be attributable to the slip-fit between at least portions of the wire and the cannula segments, and also to a slip-fit between the overlapping portions of the cannula segments.

The length of the cannula segments may be described in terms of the coverage of the cannula over the superelastic wire. Referring to FIG. 1 or FIG. 3, the length L from the bend 125 of each cannula segment 120 to either end thereof generally extends over less than 50% of the length l of each strut 112. For example, the length L of the cannula segments 120 may range from about 25% to about 49%, or from about 33% to about 45%, of the length l of each strut 112. Preferably, each cannula segment 120 is symmetrical in shape, with the bend 125 being positioned equidistant between the ends of the cannula segment 120.

Although it may be advantageous for the cannula segments to have a generally symmetrical shape and uniform size along the superelastic wire, such symmetry and uniformity are not necessary. For example, the cannula segments may be, in another embodiment, nonsymmetric in shape; i.e., the bend of one or more of the cannula segments may not lie equidistant between the ends. In this case, the cannula segment may include a first length L1 from the bend to a first end thereof and a second length L2 from the bend to a second end thereof, corresponding to the different lengths on either side of the bend. In addition, the size of the cannula segments along the superelastic wire may not be uniform. For example, the cannula segments overlying the crests of the superelastic wire may have a first size, while the cannula segments overlying the troughs of the superelastic wire may have a second larger or smaller size. In this case, the length L of some of the cannula segments from the bends to either end thereof may exceed 50% of the length l of each strut.

The superelastic wire of the resilient ring generally has a thickness d (i.e., a wire diameter or gauge) in the range of from 0.102 mm (about 0.004 in) to about 0.305 mm (0.012 in), or from about 0.1 mm to about 0.3 mm. Each cannula segment has a wall thickness sufficient to restrain the underlying superelastic wire when the hybrid stent is crimped or expanded. The desired wall thickness of the cannula segments may be material dependent and may also depend on the thickness d of the underlying superelastic wire. In general, cannula segments of a higher wall thickness may be utilized with thicker superelastic wire. The wall thicknesses of the cannula segments may range from about 0.013 mm (0.0005 in) to about 0.038 mm (0.0015 in), or from 0.01 mm to about 0.04 mm.

Advantageously, the inner diameter of the cannula segments is large enough to allow for relative motion between the superelastic wire and the cannula segments. Having sufficient clearance between the outer diameter (OD) of the superelastic wire and the inner diameter (ID) of the cannula segments may be particularly important near the gaps, where torsion of the superelastic wire may be at a maximum under crushing loads. At a minimum, the clearance between the OD of the superelastic wire and the ID of the cannula segments is larger than the tolerance of the OD of the wire added to the tolerance of the ID of the cannula segments. The clearance may also be larger. For example, the clearance may lie between about 0.01 mm and 0.04 mm. Accordingly, torsional motion of the superelastic wire under crushing loads may occur independently from the cannula segments.

Preferably, a cannula segment overlies every crest and trough of the resilient ring. There is no limit to the number of crests or troughs that may be formed in the hybrid stent. Nor is there any limit to the French size or strut length of the hybrid stent.

In addition to simulating hybrid stent structures with finite element methods, as described above, the inventors have constructed prototypes of actual hybrid stents. FIG. 2 is a representation of one exemplary prototype hybrid stent 200. The prototype 200 is fabricated from stainless steel cannula segments 120 of about 0.018 cm (about 0.007 in) in outer diameter over a nickel-titanium superelastic wire 102 of about 0.011 cm (about 0.0045 in) in diameter. The length l of the struts between the crests 110 and troughs 115 is about 2.5 mm, and the crests 110 and troughs 115 include a radius of about 0.35 mm. The prototype stent can be crimped to a 7 Fr size.

To fabricate the hybrid stents, a malleable continuous cannula (thin-walled tubing) may be cut into segments using, for example, a laser or a mechanical cutting tool. The segments may be bent to the desired radius to form what will be the crests and troughs of the hybrid stent using a mandrel of the desired radius (e.g., about 0.35 mm in the above example). The superelastic wire may then be threaded through each cannula segment one at a time. The threading may occur before or after the segments are bent to the desired radius. Once all of the cannula segments have been placed over the wire, ends of the superelastic wire may be bonded together to form the hybrid stent.

In another embodiment, the continuous cannula may be formed into the crest and trough (or "Z-stent") configuration described above and a superelastic wire may be threaded through the continuous cannula prior to cutting the continuous cannula to form the cannula segments. The continuous cannula may then be cut at each mid-strut location without cutting the interior wire using, for example, a laser or mechanical cutting tool. A single cut may be employed at each mid-strut location to segment the cannula and create a gap of a minimal size, or two cuts of a predetermined separation may be used to create a larger gap. (After making the two cuts, additional cuts may be used to remove the excess cannula material from the gap region.) Thus, the superelastic wire remains continuous while the malleable cannula is segmented. The assembly is held together by frictional forces generated by the elastic forces in the wire as it is threaded through the bends of the cannula. Ends of the superelastic wire may be bonded together using bonding methods known in the art to form the hybrid stent.

In both examples described above, the underlying superelastic wire may be stressed as it accommodates the bends of the continuous cannula or of the discrete cannula segments, and thus a heat treatment may be desired to remove or reduce these stresses after fabrication of the stent.

In yet another example of an approach for fabricating the hybrid stent, a straight superelastic wire may be threaded through a straight malleable continuous cannula, and then the bends of the cannula may be formed from the composite structure. At the mid-strut (or other) locations, the continuous cannula may be cut as described above to create the cannula segments. Ends of the wire may be bonded together to define a circumference of the stent.

It is also envisioned, in the case where the resilient ring 105 is formed from a seamless superelastic wire, such as a flat wire cut from a thin-walled tube, that the malleable cannula segments may have a discontinuous transverse cross-section (e.g., a C-shape) so as to facilitate application over the wire. According to this embodiment, the cannula segments may be applied over the superelastic wire and then deformed to take on the requisite shape and fit about the wire.

Once fabricated, the hybrid stent may undergo a heat setting treatment to impart a desired remembered shape to the resilient ring. The desired remembered shape is generally a radially expanded configuration of the hybrid stent suitable for deployment in a body vessel. It is this shape that is recovered upon removal of a crushing force. Internal stresses generated in the wire during assembly of the stent may also be removed or reduced by the heat setting treatment. During heat setting, the superelastic wire is constrained in the configuration of interest and then heated at a temperature in the range of from about 350° C. to about 550° C. The heat setting treatment may be carried out for a duration of from about 10 minutes to about 60 minutes. These conditions are generally suitable for imparting a remembered shape to nickel-titanium shape memory alloys.

The superelasticity of the wire is advantageously manifest at body temperature so that the hybrid stent may rebound from crushing blows experienced in vivo. Accordingly, nickel-titanium shape memory alloys that may be useful for the superelastic wire have an austenite finish temperature, $A_f$, which is at or below body temperature (37° C.). When at a temperature at or above $A_f$, a nickel-titanium shape memory alloy is substantially entirely austenitic. Thus, a crushing blow imparted to the ring may cause a portion of the alloy to transform to martensite and deform (e.g., mid-sections of the struts may torque) to accommodate the stress, followed by a return transformation to austenite when the stress is removed, resulting in recovery of the original undeformed configuration (e.g., un-twisting of the struts).

As noted above, the malleable cannula segments and the superelastic wire may be held together by a frictional fit, particularly in the vicinity of the bends or apices of the stent. If a more secure bond between the cannula segments and the superelastic wire is desired, then laser welding or other bonding methods known in the art may be employed to create the bond between the cannula segments and the wire at one or more suitable locations (e.g., the apices or bends) away from the gaps. For the hybrid stent to exhibit the elastic recovery described above under crushing loads, it is desirable that the cannula segments are free to rotate with respect to the superelastic wire in the vicinity of the gap regions. Thus, a sliding interface between the cannula segments and superelastic wire is advantageous in the regions near the gaps.

The preferred embodiments use cannulae of malleable material which overlie a stent wire of superelastic material. It is envisaged, however, that some embodiments will use a reinforcement which is not of cannula form but of other elongate form which overlies the superelastic wire over at least a part of the circumference of the wire. For instance, the reinforcement could be in the form of an elongate strip of material or could be of a part circumferential shape. The reinforcement acts to distribute stress over the stent ring, particularly at the peaks and troughs.

A hybrid stent that exploits both plastic and superelastic modes of deformation for deployment and use in a body vessel has been described. The hybrid stent is plastically deformed for crimping and balloon expansion but exhibits superelastic recovery in response to crushing forces experienced in vivo. The inventors believe the hybrid stent is well-suited to applications in the superficial femoral artery (SFA), the carotid artery, and other vessels that may be deformed or collapsed by external forces. A stent deployed in these locations undergoes considerable motion, especially in axial, bending, and torsion modes, and may be exposed to various exterior loads over its lifetime that require resiliency if the stent is to remain viable in the vessel.

It is envisaged that the cannula need not be slipped onto the superelastic wire but may be radially fitted thereto, for instance by means of a longitudinally extending cut in the cannula allowing fitting in a radial direction.

Although various embodiments have been described in considerable detail, the skilled person will appreciate that the teachings herein are not limited to those embodiments only. Other embodiments are possible within the scope of the teachings herein and of the appended claims. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A hybrid stent including:
   at least one resilient ring, wherein each of the at least one resilient rings comprises a superelastic wire formed in a sinusoidal pattern of alternating crests and troughs about a ring circumference; and
   a plurality of malleable segments overlying the superelastic wire at the crests and troughs, each of the segments comprising a bend and having an inner diameter sized to allow relative motion between at least a portion of the wire and the segment,
   wherein deformation of the segments dominates a response of the stent to substantially uniform radial forces, and deformation of the at least one resilient ring dominates a response of the stent to radially nonuniform crushing forces.

2. The hybrid stent according to claim 1, including a plurality of gaps wherein each gap is formed by a spacing between opposing segments.

3. The hybrid stent according to claim 2, wherein the spacing between the opposing segments from 1% to 25% of a length of a stent strut, the stent strut being a portion of the superelastic wire extending between an opposing crest and trough.

4. The hybrid stent according to claim 1, wherein each segment is in the form of a cannula.

5. The hybrid stent according to claim 1, wherein the segments overlie the superelastic wire at every crest and trough.

6. The hybrid stent according to claim 1, wherein the segments have a symmetric shape.

7. The hybrid stent according to claim 1, wherein one or more of the segments have a length L from the bend to either end that extends over less than 50% of a length of a stent strut, the stent strut being a portion of the superelastic wire extending between an opposing crest and trough.

8. The hybrid stent according to claim 1, wherein the superelastic wire has a thickness d of between 0.1 mm and 0.3 mm.

9. The hybrid stent according to claim 1, wherein one or more of the segments has a wall thickness of between 0.01 mm and 0.04 mm.

10. The hybrid stent according to claim 1, wherein a clearance between the inner diameter of the segments and an outer diameter of the superelastic wire is between 0.01 mm and 0.04 mm.

11. The hybrid stent according to claim 1, wherein the superelastic wire comprises a round wire having ends joined together to define the ring circumference.

12. The hybrid stent according to claim 1, wherein the superelastic wire comprises a seamless flat wire cut from a thin-walled tube.

13. The hybrid stent according to claim 1, wherein the superelastic wire comprises a nickel-titanium alloy and wherein the segments comprise a stainless steel alloy.

14. The hybrid stent according to claim 1, including a plurality of the at least one resilient rings arranged along a longitudinal axis.

15. The hybrid stent according to claim 14, including a plurality of interconnecting segments joining longitudinally adjacent rings.

16. The hybrid stent according to claim 15, wherein the interconnecting segments are biodegradable.

17. The hybrid stent according to claim 1, wherein the segments overlie the superelastic wire at every crest and trough and have a symmetric shape, the stent comprising a plurality of gaps, wherein each gap is defined by a spacing between opposing segments, the spacing between opposing segments being from 1% to 25% of a length of a stent strut, the stent strut being a portion of the superelastic wire extending between an opposing crest and trough, wherein the superelastic wire has a thickness cf of between 0.1 mm and 0.3 mm and the segments have a wall thickness of between 0.01 mm and 0.04 mm, wherein a clearance between the inner diameter of the segments and an outer diameter of the superelastic wire is between 0.01 mm and 0.04 mm, wherein the superelastic wire comprises a round wire having ends joined together to define a ring circumference, and wherein the superelastic wire comprises a nickel-titanium alloy and the segments comprise a stainless steel alloy.

* * * * *

UNITED STATES PATENT AND TRADEMARK OFFICE
CERTIFICATE OF CORRECTION

PATENT NO. : 8,679,173 B2  Page 1 of 1
APPLICATION NO. : 13/257073
DATED : March 25, 2014
INVENTOR(S) : Dierking et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 118 days.

Signed and Sealed this

Twenty-ninth Day of September, 2015

Michelle K. Lee
*Director of the United States Patent and Trademark Office*